(12) United States Patent
Chen et al.

(10) Patent No.: US 6,403,599 B1
(45) Date of Patent: *Jun. 11, 2002

(54) CORTICOTROPIN RELEASING FACTOR ANTAGONISTS

(75) Inventors: Yuhpyng L. Chen, Waterford; Anthony A. Fossa, Mystic, both of CT (US)

(73) Assignee: Pfizer Inc, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/741,066

(22) Filed: Oct. 30, 1996

Related U.S. Application Data

(63) Continuation of application No. 08/741,066, filed on Oct. 30, 1996.
(60) Provisional application No. 60/006,333, filed on Nov. 8, 1995.

(51) Int. Cl.[7] .................... A61K 31/505; A61K 31/41; A61K 31/40
(52) U.S. Cl. .................... 514/269; 514/272; 514/275; 514/381; 514/415
(58) Field of Search .................... 514/269, 272, 514/275, 381, 415

(56) References Cited

FOREIGN PATENT DOCUMENTS

| WO | WO 94/13643 | 6/1994 |
|---|---|---|
| WO | WO 94/13644 | 6/1994 |
| WO | WO 94/13661 | 6/1994 |
| WO | WO 94/13676 | 6/1994 |
| WO | WO 94/13677 | 6/1994 |
| WO | WO 95/34563 | 3/1995 |
| WO | WO 95/33750 | 12/1995 |

OTHER PUBLICATIONS

L.A. Fisher, Central Actions of Corticotropin–Releasing Factor on Autonomic Nervous Activity and Cardiovascular Functioning, 1993 Corticotropin–Releasing Factor, CIBA Found. Symposium 172, pp. 243–257.
M.R. Brown et al., Endocrinology 111:928, 1982.
J.M. Overton et al., Journal of the Autonomic Nervous System, 35 (1991) 43–52.
M.R. Brown et al., Life Sciences, vol. 30, No. 2, pp. 207–210 (1982).
L.S. Fisher et al., Endocrinology 110(6), 2222–2224, 1982.
C.L. Grosskreutz et al., Brain Research, 442 (1988) 363–367.
M.R. Brown et al., Brain Research, 280 (1983) 75079.
J.M. Overton et al., Central Nervous System Effects of CRF and Angiotensin II on Cardiac Output in Conscious Rats, J. Appl. Physiol. 69(2):788–791, 1990.
H. Lehnert et al., Neuropsychobiology, 28:54–61 (1993).
A. Wiersma et al., Brain Research, 625 (1993) 219–227.
A.L. Curtis et al., Brain Res. Bulletin, vol. 31, pp. 737–744, 1993.
Abstract of E. Rohde et al., Biochemical Pharmacology, 52(6):829–833, Sep. 27, 1996.
R.J. Valentino et al, Brain Research, 555 (1991) 25–34.
R.J. Valentino et al, Neuroendocrinology, 48:674–677 (1988).
T. Nakamori et al., Am. J. Physiol., 265: R834–R839, 1993.
G.S. Francis et al., Circulation, 87 (Suppl. VI): V140–V148, 1993.

Primary Examiner—Theodore J. Criares
(74) Attorney, Agent, or Firm—Peter C. Richardson; Paul H. Ginsburg; Bryan C. Zielinski

(57) ABSTRACT

A method of treating, preventing or inhibiting a disorder selected from the group consisting of cardiovascular or heart related diseases such as stroke, hypertension, tachycardia, and congestive heart failure, osteoporosis, premature birth, psychosocial dwarfism, stress-induced fever, ulcer, diarrhea, post-operative ileus, and colonic hypersensitivity associated with psychopathological disturbance and stress, comprising administering to a mammal, including a human, in need of such treatment a therapeutically effective amount of a compound of the formula

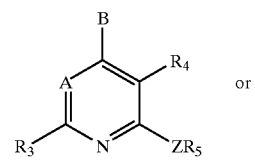

I or

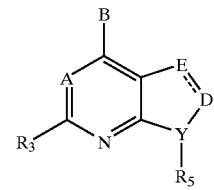

II or a pharmaceutically acceptable salt thereof, wherein A, B, D, E, Y, Z, $R_3$, $R_4$, and $R_5$ are as defined herein.

13 Claims, No Drawings

CORTICOTROPIN RELEASING FACTOR ANTAGONISTS

This application is a continuation of U.S. patent application Ser. No. 08/741,066, filed Oct. 30, 1996, which claims priority from U.S. Provisional Patent Application Serial No. 60/006,333, filed Nov. 8, 1995, which applications are incorporated herein by reference.

BACKGROUND OF THE INVENTION

The present invention relates to the treatment of certain conditions using a compound of formula I or II, or a pharmaceutically acceptable salt thereof, as defined below. Specifically, the compounds of formulas I and II, and their pharmaceutically acceptable salts, as defined below, exhibit corticotropin-releasing factor (CRF) antagonist activity and are useful in the treatment of cardiovascular or heart related diseases such as hypertension, tachycardia, and congestive heart failure, stroke, osteoporosis, premature birth, psychosocial dwarfism, stress-induced fever, ulcer, diarrhea, post-operative ileus, and colonic hypersensitivity associated with psychopathological disturbance and stress.

The compounds of formulas I and II, their pharmaceutically acceptable salts, and methods of preparing such compounds and salts are referred to in copending PCT international patent application numbers PCT/IB95/00373 (filed May 18, 1995) and PCT/IB95/00439 (filed Jun. 6, 1995), both of which designate the United States, and in copending U.S. patent applications Ser. No. 08/448,539 (filed Jun. 14, 1995) and Ser. No. 08/481,413 (filed Jun. 15, 1995). PCT international patent application numbers PCT/IB95/00373 and PCT/IB95/00439, and U.S. patent application Ser. Nos. 08/448,539 and 08/481,413, referred to above, are incorporated herein by reference in their entirety.

The foregoing PCT international patent applications and United States patent applications refer to the use of the compounds of formulas I and II in the treatment of illnesses induced or facilitated by corticotropin releasing factor and in the treatment of anxiety, depression, fatigue syndrome, gastrointestinal diseases, headache, pain, cancer, immune dysfunction, hemorrhagic stress, drug addiction, drug and alcohol withdrawal symptoms, fertility problems, stress-induced psychotic episodes, neurodegenerative diseases such as Alzheimer's disease; irritable bowel syndrome including Crohn's disease, spastic colon and irritable colon; eating disorders such as anorexia nervosa; and inflammatory disorders such as arthritis, asthma and allergies.

Other CRF antagonists that can be used to treat the disorders recited in the method of this invention are referred to in copending PCT international patent application number PCT/IB95/00318 (filed May 4, 1995), which designates the United States, and in copending U.S. patent application Ser. No. 08/448,534 (filed Jun. 14, 1995) and Ser. No. 08/448,529 (filed Jun. 14, 1995). PCT international patent application number PCT/IB95/00318, and U.S. patent application Ser. Nos. 08/448,534 and 08/448,529, referred to above, are incorporated herein by reference in their entirety.

CRF antagonists are mentioned in U.S. Pat. Nos 4,605,642 and 5,063,245 referring to peptides and pyrazolinones, respectively. The importance of CRF antagonists is set out in the literature, e.g., as discussed in U.S. Pat. No. 5,063,245, which is incorporated herein by reference. A recent outline of the different activities possessed by CRF antagonists is found in M. J. Owens et al., *Pharm. Rev., Vol.* 43, pages 425 to 473 (1991), also incorporated herein by reference.

SUMMARY OF THE INVENTION

This invention relates to a method of treating a disorder selected from cardiovascular or heart related diseases such as hypertension, tachycardia, and congestive heart failure, osteoporosis, premature birth, psychosocial dwarfism, stress-induced fever, ulcer, diarrhea, post-operative ileus, and colonic hypersensitivity associated with psychopathological disturbance and stress, by administering to a mammal, including a human, In need of such treatment a therapeutically effective amount of a compound of the formula

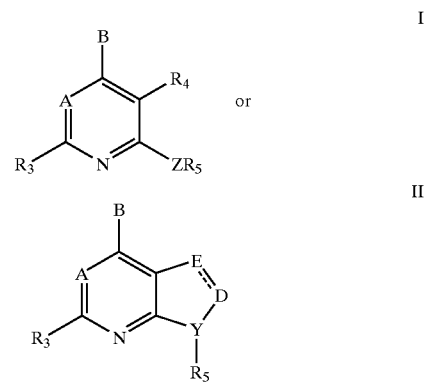

or a pharmaceutically acceptable salt thereof, wherein
the dashed line represents an optional double bond;
A is —$CR_7$ or N;
B is —$NR_1R_2$, —$CR_1R_2R_{11}$, —$C(=CR_1R_{12})R_2$, —$NHCR_{11}R_1R_2$, —$OCR_{11}R_1R_2$, —$SCR_{11}R_1R_2$, —$CR_{11}R_2OR_1$, —$CR_{11}R_2SR_1$, —$C(S)R_2$, —$NHNR_1R_2$, —$CR_2R_{11}NHR_1$ or —$C(O)R_2$;
D is: (i) N or —$CR_{10}$ when a double bond connects E and D and E is —$CR_4$; (ii) —$CR_{10}$ when a double bond connects E and D and E is N; (iii) —$CR_8R_9$, —$CHR_{10}$, —C=O, —C=S, —C=NH, or —$C=NCH_3$ when a single bond connects E and D;
E is —$CR_4$ or N when a double bond connects E and D, and E is —$CR_4R_6$ or —$NR_6$ when a single bond connects E and D;
Y is N or —CH;
Z is NH, O, S, —$N(C_1-C_2$ alkyl) or —$CR_{12}R_{13}$, wherein $R_{12}$ and $R_{13}$ are each, independently, hydrogen, trifluoromethyl or methyl, or one of $R_{12}$ and $R_{13}$ is cyano and the other is hydrogen or methyl;
$R_1$ is hydrogen or $C_1-C_6$ alkyl which is optionally substituted with one or two substituents independently selected from hydroxy, cyano, nitro, fluoro, chloro, bromo, iodo, $CF_3$, $C_1-C_4$ alkoxy, —O—CO—($C_1-C_4$ alkyl), —O—CO—NH($C_1-C_4$ alkyl), —O—CO—N($C_1-C_4$ alkyl)($C_1-C_2$ alkyl), —NH($C_1-C_4$ alkyl), —N($C_1-C_2$ alkyl)($C_1-C_4$ alkyl), —S($C_1-C_4$ alkyl), —N($C_1-C_4$alkyl)CO($C_1-C_4$ alkyl), —NHCO($C_1-C_4$ alkyl), —$CO_2$($C_1-C_4$ alkyl), —CONH($C_1-C_4$ alkyl), —CON($C_1-C_4$ alkyl)($C_1-C_2$ alkyl), ($C_1-C_4$ alkyl)sulfinyl, ($C_1-C_4$ alkyl)sulfonyl, and ($C_1-C_4$ alkyl)sulfanyl, and wherein said $C_1-C_6$ alkyl, $C_1-C_4$ alkoxy and the $C_1-C_4$ alkyl moieties in the foregoing $R_1$ groups optionally contain one double or triple bond;
$R_2$ is $C_1-C_6$ alkyl, aryl or (aryl)$C_1-C_4$ alkyl wherein said aryl and the aryl moiety of said (aryl)$C_1-C_4$ alkyl are selected from the group consisting of phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, and benzoxazolyl; or $R^2$ is $C_3$–$C_8$ cycloalkyl or ($C_3$–$C_8$ cycloalkyl) $C_1$–$C_6$ alkyl, wherein one or two of the ring carbons of said cycloalkyl having at least 4 ring members and the cycloalkyl moiety of said ($C_3$–$C_8$ cycloalkyl)$C_1$–$C_6$ alkyl having at least 4 ring members is optionally replaced by an oxygen or sulfur atom or by —$NR_{14}$ wherein $R_{14}$ is hydrogen or $C_1$–$C_4$ alkyl; and wherein each of the foregoing $R_2$ groups is optionally substituted by from one to three substituents independently selected from chloro, fluoro and $C_1$–$C_4$ alkyl, or by one substituent selected from bromo, iodo, cyano, nitro, $C_1$–$C_6$ alkoxy, —O—CO—($C_1$–$C_4$ alkyl), —O—CO—N($C_1$–$C_4$ alkyl)($C_1$–$C_2$ alkyl), —$CO_2$($C_1$–$C_4$ alkyl), ($C_1$–$C_4$ alkyl)sulfanyl, ($C_1$–$C_4$ alkyl)sulfinyl, and ($C_1$–$C_4$ alkyl)sulfonyl, and wherein said $C_1$–$C_6$ alkyl and the $C_1$–$C_4$ alkyl and $C_1$–$C_6$ alkyl moieties of the foregoing $R_2$ groups optionally contain one carbon-carbon double or triple bond;

or $R^1$ and $R^2$ of said —$NR_1R_2$ and said —$CR_1R_2R_{11}$ are taken together to form a saturated 5 to 8 member ring, wherein said ring optionally contains one or two carbon-carbon double bonds, and wherein one or two of the ring carbons is optionally replaced by an oxygen or sulfur atom;

$R_3$ is hydrogen, $C_1$–$C_6$ alkyl, fluoro, chloro, bromo, iodo, hydroxy, amino, SH, —NH($C_1$–$C_4$ alkyl), —N($C_1$–$C_4$ alkyl)($C_1$–$C_2$ alkyl), —$CH_2OH$, —$CH_2OCH_3$, —O($C_1$–$C_4$ alkyl), ($C_1$–$C_4$ alkyl)sulfanyl, ($C_1$–$C_4$ alkyl)sulfonyl, or ($C_1$–$C_4$ alkyl)sulfinyl, wherein said $C_1$–$C_6$ alkyl and the $C_1$–$C_4$ alkyl moieties of the foregoing $R_3$ groups optionally contain one double or triple bond and are optionally substituted by from one to three substituents independently selected from hydroxy, amino, $C_1$–$C_3$ alkoxy, —NH($C_1$–$C_2$ alkyl), —N($C_1$–$C_2$)$_2$, —NHCOCH$_3$, fluoro, chloro and $C_1$–$C_3$ thioalkyl;

$R_4$ is hydrogen, $C_1$–$C_6$ alkyl, fluoro, chloro, bromo, iodo, $C_1$–$C_6$ alkoxy, formyl, trifluoromethoxy, —$CH_2OCH_3$, —$CH_2OCH_2CH_3$, —$CH_2CH_2OCH_3$, —$CH_2CF_3$, $CF_3$, amino, nitro, —NH($C_1$–$C_4$ alkyl), —N($CH_3$)$_2$, —NHCOCH$_3$, —NHCONHCH$_3$, ($C_1$–$C_4$ alkyl)sulfanyl, ($C_1$–$C_4$ alkyl)sulfinyl, ($C_1$–$C_4$ alkyl)sulfonyl, cyano, hydroxy, —CO($C_1$–$C_4$ alkyl), —CHO, or —$CO_2$($C_1$–$C_4$ alkyl), wherein said $C_1$–$C_6$ alkyl, $C_1$–$C_6$ alkoxy and the $C_1$–$C_4$ alkyl moieties of the foregoing $R_4$ groups optionally contain one double or triple bond and are optionally substituted with one substituent selected from hydroxy, amino, —NHCOCH$_3$, —NH($C_1$–$C_2$ alkyl), —N($C_1$–$C_2$ alkyl)$_2$, —$CO_2$($C_1$–$C_4$ alkyl), —CO($C_1$–$C_4$ alkyl), $C_1$–$C_3$ alkoxy, ($C_1$–$C_3$ alkyl)sulfanyl, fluoro, chloro, cyano and nitro;

$R_5$ is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, pyridinyl, tetrazolyl, or 3- to 8-membered cycloalkyl or 9- to 12-membered bicycloalkyl, wherein said cycloalkyl and bicycloalkyl optionally contain one or two of O, S or —N—G wherein G is hydrogen, $C_1$–$C_4$ alkyl, $C_1$–$C_4$ alkanoyl, phenyl or benzyl, wherein each of the above $R_5$ groups is optionally substituted by from one to three substituents independently selected from fluoro, chloro, $C_1$–$C_6$ alkyl, $C_1$–$C_6$ alkoxy and trifluoromethyl, or one substituent selected from bromo, iodo, cyano, nitro, amino, —NH($C_1$–$C_4$ alkyl), —N($C_1$–$C_4$ alkyl)($C_1$–$C_2$ alkyl), —$CO_2$($C_1$–$C_4$ alkyl), —CO($C_1$–$C_4$ alkyl), —$SO_2NH$($C_1$–$C_4$ alkyl), —$SO_2N$($C_1$–$C_4$ alkyl)($C_1$–$C_2$ alkyl), —$SO_2NH_2$, —$NHSO_2$($C_1$–$C_4$ alkyl), —S($C_1$–$C_4$ alkyl), and —$SO_2$($C_1$–$C_4$ alkyl), wherein said $C_1$–$C_4$ alkyl and $C_1$–$C_6$ alkyl moieties of the foregoing $R_5$ groups optionally contain one double or triple bond and are optionally substituted by one or two substituents independently selected from fluoro, chloro, hydroxy, amino, methylamino, dimethylamino and acetyl;

$R_6$ is hydrogen or $C_1$–$C_6$ alkyl, wherein said $C_1$–$C_6$ alkyl is optionally substituted by a single hydroxy, methoxy, ethoxy or fluoro group;

$R_7$ is hydrogen, $C_1$–$C_4$ alkyl, fluoro, chloro, bromo, iodo, cyano, hydroxy, $C_1$–$C_4$ alkoxy, —CO($C_1$–$C_4$ alkyl), —$CO_2$($C_1$–$C_4$ alkyl), —$OCF_3$, $CF_3$, —$CH_2OH$, —$CH_2OCH_3$ or —$CH_2OCH_2CH_3$;

$R_8$ and $R_9$ are each, independently, hydrogen, hydroxy, methyl, ethyl, methoxy, or ethoxy;

or $R_8$ and $R_9$ together form an oxo (=O) group;

$R_{10}$ is hydrogen, $C_1$–$C_6$ alkyl, fluoro, chloro, bromo, iodo, $C_1$–$C_6$ alkoxy, formyl, amino, —NH($C_1$–$C_4$ alkyl), —N($C_1$–$C_4$ alkyl)($C_1$–$C_2$ alkyl), —$SO_n$($C_1$–$C_4$ alkyl), wherein n is 0, 1 or 2, cyano, carboxy, or amido, wherein said $C_1$–$C_6$ alkyl and the $C_1$–$C_4$ alkyl moieties of the foregoing $R_{10}$ groups are optionally substituted by one of hydroxy, trifluoromethyl, amino, carboxy, amido, —NHCO($C_1$–$C_4$ alkyl), —NH($C_1$–$C_4$ alkyl), —N($C_1$–$C_4$ alkyl)($C_1$–$C_2$ alkyl), —$CO_2$($C_1$–$C_4$ alkyl), $C_1$–$C_3$ alkoxy, $C_1$–$C_3$ thioalkyl, fluoro, bromo, chloro, iodo, cyano or nitro; and, $R_{11}$ is hydrogen, hydroxy, fluoro, or methoxy.

The term "alkyl", as used herein, unless otherwise indicated, includes saturated monovalent hydrocarbon radicals having straight or branched moieties or combinations thereof.

The term "alkoxy", as used herein, unless otherwise indicated, includes O-alkyl groups wherein "alkyl" is defined above.

The term "treatment", as used herein, unless otherwise indicated, includes the treatment, prevention, or inhibition of any disorder enumerated within the method of the invention.

More specific compounds for use in the method of the invention include compounds of formula I or II, or pharmaceutically acceptable salts thereof, wherein: B is —$NR_1R_2$, —NHCHR$_1R_2$, —CR$_1R_2R_{11}$, —SCHR$_1R_2$ or —OCHR$_1R_2$; $R_1$ is $C_1$–$C_6$ alkyl which is optionally substituted with a single hydroxy, fluoro or $C_1$–$C_2$ alkoxy group and optionally contains one carbon-carbon double or triple bond; $R_2$ is benzyl or $C_1$–$C_6$ alkyl which optionally contains one carbon-carbon double or triple bond, wherein said $C_1$–$C_6$ alkyl and the phenyl moiety of said benzyl are optionally substituted with fluoro, $C_1$–$C_2$ alkyl, or $C_1$–$C_2$ alkoxy; and $R_{11}$ is hydrogen or fluoro.

Other more specific compounds for use in the method of the invention include compounds of formula I or II, or pharmaceutically acceptable salts thereof, wherein $R_2$ is (aryl)$C_1$–$C_4$ alkyl in which said aryl moiety is phenyl, thienyl, benzofuranyl, furanyl, benzothienyl, thiazolyl, pyridyl or benzothiazolyl.

Other more specific compounds for use in the method of the invention include compounds of formula I or II, or pharmaceutically acceptable salts thereof, wherein B is —$NR_1R_2$ or —CHR$_1R_2$ in which $R_1$ and $R_2$ are taken together with N or CH to form a 5- or 6-membered ring optionally having sulfur, oxygen, or one more nitrogen in said ring, such as a pyrrolidinyl, pyrrolyl, pyrazolyl, imidazolyl, oxazolyl, thiazolyl, isoxazolyl, thiadiazolyl, oxadiazolyl, pyridyl, pyrazinyl or pyrimidyl group.

Other more specific compounds for use in the method of the invention include compounds of formula I or II, or pharmaceutically acceptable salts thereof, wherein B is —NHCHR$_1$R$_2$ or —OCHR$_1$R$_2$, wherein the CHR$_1$R$_2$ moiety is a 5- or 6-membered ring which optionally contains one oxygen or sulfur, such as a tetrahydrofuranyl, tetrahydrothiafuranyl or cyclopentanyl group.

Other more specific compounds for use in the method of the invention include compounds of formula I or II, or pharmaceutically acceptable salts thereof, wherein B is tetrahydrofuranyl, tetrahydrothienyl or thiazolidinyl.

Other more specific compounds for use in the method of the invention include compounds of formula I or II, or pharmaceutically acceptable salts thereof, wherein R$_3$ is methyl, chloro, or methoxy; R$_4$ is methyl, —CH$_2$OH, cyano, trifluoromethoxy, methoxy, trifluoromethyl, chloro, —CO$_2$CH$_3$, —CH$_2$OCH$_3$, —CH$_2$Cl, —CH$_2$F, amino or nitro; R$_6$ is hydrogen, methylsulfinyl, methylsulfanyl, methylsulfonyl, methyl or ethyl; and R$_5$ is phenyl or pyridyl wherein said phenyl or pyridyl is substituted by two or three substituents independently selected from fluoro, chloro, bromo, iodo, C$_1$–C$_4$ alkoxy, trifluoromethyl, (C$_1$–C$_2$ alkoxy) C$_1$–C$_4$ alkyl, C$_1$–C$_3$ hydroxyalkyl, hydroxy, formyl, —CO$_2$ (C$_1$–C$_2$ alkyl), (amino)C$_1$–C$_2$ alkyl, —CO(C$_1$–C$_4$ alkyl), and C$_1$–C$_6$ alkyl, wherein said C$_1$–C$_6$ alkyl and said C$_1$–C$_4$ alkyl are optionally substituted by a single hydroxy, C$_1$–C$_2$ alkoxy or fluoro group and optionally contains one carbon-carbon double or triple bond.

For use in the method of the invention, specific compounds of formulas I and II include:
4-(1-ethyl-propoxy)-2,5dimethyl-6-(2,4,6-trimethyl-benzyl)-pyrimidine;
2-(4-bromo-2,6-dimethyl-phenoxy)-4-(1-ethyl-propoxy)-3,6-dimethyl-pyridine;
2-(4-ethyl-2,6-dimethyl-phenoxy)-4-(1-ethyl-propoxy)-3,6-dimethyl-pyridine;
3-ethyl-4-(1-ethyl-propoxy)-6-methyl-2-(2,4,6-trimethyl-phenoxy)-pyridine;
2-(2,6dimethyl-4-propyl-phenoxy)-4-(1-ethyl-propoxy)-3,6-dimethyl-pyridine;
4-(1-ethyl-propoxy)-2-(4-methoxy-2,6-dimethyl-phenoxy)-3,6-dimethyl-pyridine;
2-(4-ethoxy-2,6-dimethyl-phenoxy)-4-(1-ethyl-propoxy)-3,6-dimethyl-pyridine;
2-(4chloro-2,6-dimethyl-phenoxy)-4-(1-ethyl-propoxy)-3,6-dimethyl-pyridine;
4-(1-methoxymethyl-propoxy)-3,6-dimethyl-2-(2,4,6-trimethyl-phenoxy)-pyridine;
[3,6-dimethyl-2-(2,4,6-trimethyl-phenoxy)-pyridiny-4-yl]-diethyl-amine;
[3,6-dimethyl-2-(2,4,6-trimethyl-phenoxy)-pyridin-4-yl]-ethyl-propyl-amine;
[2,5-dimethyl-6-(2,4,6-trimethyl-phenoxy)-pyrimidin-4-yl] (1-ethyl-propyl)-amine;
butyl-[3,6-dimethyl-2-(2,4,6-trimethyl-phenoxy)-pyridin-4-yl]-ethyl-amine;
4-(1-ethyl-propoxy)-3,6-dimethyl-2-(2,4,6-trimethyl-phenylsulfanyl)-pyridine;
butyl-[2-(4-chloro-2,6-dimethyl-phenoxy)-3,6-dimethyl-pyridin-4-yl]-ethyl-amine;
4-(1-ethyl-propylamino)-6-methyl-2-(2,4,6-trimethyl-phenoxy)-nicotinic acid methyl ester;
[3,6-dimethyl-[2-(2,4,6-trimethyl-phenylsulfanyl)-pyridin-4yl-]-ethyl-propyl-amine;
4-(1-ethyl-propylamino)-6-methyl-2-(2,4,6-trimethyl-phenoxy)-pyridin-3-yl]-methanol;
[2-(4-chloro-2,6-dimethyl-phenoxy)-3,6-dimethyl-pyridin-4yl-]ethyl-propyl-amine;
1-(ethyl-propyl)-[6-methyl-3-nitro-2-(2,4,6-trimethyl-phenoxy)-pyridin4yl-]-amine;
N4-(1-ethyl-propyl)-6-methyl-3-nitro-N2-(2,4,6-trimethyl-phenyl)-pyridine-2,4-diamine;
N4-(1-ethyl-propyl)-6-methyl-2-(2,4,6-trimethyl-phenoxy)-pyridine-3,4-diamine;
N4-(1-ethyl-propyl)-6-methyl-N2-(2,4,6-trimethyl-phenyl)-pyridine-2,3,4-diamine;
[3,6-dimethyl-2-(2,4,6-trimethyl-phenoxy)-pyridin-4-yl]-ethyl-(2,2,2-trifluoro-ethyl)-amine;
[3-chloromethyl-6-methyl-2-(2,4,6-trimethyl-phenoxy) pyridin-4-yl]-(1-ethyl-propyl)-amine;
[3,6-dimethyl-2-(2,4,6-trimethyl-phenoxy)-pyridin-4-yl]-(1-ethyl-propyl)-amine;
(1-ethyl-propyl)-[2-methyl-5-nitro-6-(2,4,6-trimethyl-pyridin-3-yloxy)-pyrimidin-4-yl]-amine;
(1-ethyl-propyl)-[3-methoxymethyl-6-methyl-2-(2,4,6-trimethyl-phenoxy)-pyridin-4-yl]-amine;
N-(1-ethyl-propyl)-2-methyl-5-nitro-N'-(2,4,6-trimethyl-pyridin-3-yl)-pyrimidine-4,6-diamine;
[2-(4-chloro-2,6-dimethyl-phenoxy)-3,6-dimethylpyridin-4-yl]-diethyl-amine;
4-(1-ethyl-propoxy)-3,6-dimethyl-2-(2,4,6-trimethylphenoxy)-pyridine;
butyl-[2,5-dimethyl-7-(2,4,6-trimethylphenyl)-6,7-dihydro-5H-pyrrolo[2,3-d]pyrimidin-4-yl]-ethyl-amine;
4-(butyl-ethylamino)-2,5-dimethyl-7-(2,4,6-trimethylphenyl)-5,7-dihydro-pyrrolo[2,3-d]pyrimidin-6-one;
4-(1-ethylpropoxy)-2,5-dimethyl-6-(2,4,6-trimethylphenoxy)-pyrimidine;
N-butyl-N-ethyl-2,5-dimethyl-N'-(2,4,6-trimethylphenyl)-pyrimidine-4,6-diamine;
(1-ethyl-propyl)-[5-methyl-3-(2,4,6-trimethyl-phenyl)-3H-imidazo[4,5-b]pyridin-7-yl]amine;
[2,5-dimethyl-3-(2,4,6-trimethyl-phenyl)-3H-imidazo[4,5-b]pyridin-7-yl]-(1-ethyl-propyl)-amine;
N4-(1-ethyl-propyl)-6, N3-dimethyl-2-(2,4,6-trimethyl-phenoxy)pyridine-3,4-diamine;
N4-(1-ethyl-propyl)-6,N3,N3-trimethyl-2-(2,4,6-trimethyl-phenoxy)-pyridine-3,4-diamine;
6-(1-ethyl-propoxy)-2-methyl-N4-(2,4,6-trimethyl-phenyl)-pyridine-4,5-diamine;
[4-(1-ethyl-propoxy)-3,6-dimethyl-pyridin-2-yl]-(2,4,6-trimethylphenyl)-amine; and
6-(ethyl-propyl-amino)-2,7-dimethyl-9-(2,4,6-trimethylphenyl)-7,9-dihydro-purin-8-one.

For use in the method of the invention, specific compounds of formula II wherein E and D are connected by a double bond, E is —CR$_4$, D is —CR$_{10}$ or N, Y is N, and A is —CR$_7$, include:
butyl-[3,6-dimethyl-1-(2,4,6-trimethylphenyl)-1H-pyrazolo[3,4-b]pyridin-4-yl]-ethylamine;
3,6-dimethyl-4-(tetrahydrofuran-3-yloxy)-1-(2,4,6-trimethylphenyl)-1H-pyrazolo[3,4-b]pyridine;
[3,6-dimethyl-1-(2,4,6-trimethylphenyl)-1H-pyrazolo[3,4,b]pyridin-4-yl]-(1-methoxymethylpropyl)-amine;
4-(1-methoxymethylpropoxy)-3,6-dimethyl-1-(2,4,6-trimethylphenyl)-1H-pyrazolo[3,4-b]pyridine;
(1-ethylpropyl)-[3,5,6-trimethyl-1-(2,4,6-trimethylphenyl)-1H-pyrazolo[3,4-b]pyridin-4-yl]-amine;
4-(1-ethylpropoxy)-2,5-dimethyl-7-(2,4,6-trimethylphenyl)-7H-pyrrolo[2,3-b]pyridine;

4-(1-ethylpropoxy)-2,5,6-trimethyl-7-(2,4,6-trimethylphenyl)-7H-pyrrolo[2,3b]pyridine; and 4-(1-ethylpropoxy)-2,5-dimethyl-7-(2,6-dimethyl-4-bromophenyl)-7H-pyrrolo[2,3-b]pyridine.

For use in the method of the invention, specific compounds of formula II wherein E and D are connected by a double bond, E is —CR$_4$, and D, Y and A are N, include:

3-{(4-methyl-benzyl)-[3,6-dimethyl-1-(2,4,6-trimethylphenyl)-1H-pyrazolo[3,4-d]pyrimidin-4-yl]-amino}-propan-1-ol;

diethyl-[6-methyl-3-methylsulfanyl-1-(2,4,6-trichlorophenyl)-1H-pyrazolo[3,4-d]pyrimidin-4-yl]-amine;

2-{butyl-[6-methyl-3-methylsulfanyl-1-(2,4,6-tichlorophenyl)-1H-pyrazolo[3,4-d]pyrimidin-4-yl]amino}-ethanol;

dibutyl-[6-methyl-3-methylsulfanyl-1-(2,4,6-trichlorophenyl)-1H-pyrazolo[3,4-d]pyrimidin-4-yl}-amine;

butyl-ethyl-[6-methyl-3-methylsulfanyl-1-(2,4,6-trichlorophenyl)-1H-pyrazolo[3,4-d]pyrimidin-4-yl]-amine;

butyl-ethyl-[6-methyl-3-methylsulfonyl-1-(2,4,6-trichlorophenyl)-1H-pyrazolo[3,4-d]pyrimidin-4-yl]-amine;

butyl-cyclopropylmethyl-[6-methyl-3-methylsulfanyl-1-(2,4,6-trichlorophenyl)-1H-pyrazolo[3,4-d]pyrimidin-4-yl]-amine;

di-1-propyl-[6-methyl-3-methylsulfanyl-1-(2,4,6-trichlorophenyl)-1H-pyrazolo[3,4-d]pyrimidin-4-yl]-amine;

dially-[6-methyl-3-methylsulfanyl-1-(2,4,6-trichlorophenyl)-1H-pyrazolo[3,4-d]pyrimidin-4-yl]-amine;

butyl-ethyl-[6-chloro-3-methylsulfanyl-1-(2,4,6-trichlorophenyl)-1H-pyrazolo[3,4-d]pyrimidin-4-yl]-amine;

butyl-ethyl-[6-methoxy-3-methylsulfanyl-1-(2,4,6-trichlorophenyl)-1H-pyrazolo[3,4-d]pyrimidin-4-yl]-amine;

propyl-ethyl-[3,6-dimethyl-1-(2,4,6-trimethylphenyl)-1H-pyrazolo[3,4-d]pyrimidin-4-yl]-amine;

4-(1-ethyl-propyl)-6-methyl-4-methylsulfanyl-1-(2,4,6-trimethylphenyl)-1H-pyrazolo[3,4-d]pyrimidine;

2-[3,6dimethyl-1-(2,4,6-trimethylphenyl)-1H-pyrazolo[3,4-d]pydmidin-4-ylamine]-butan-1-ol;

[3,6-dimethyl-1-(2,4,6-trimethylphenyl)-1H-pyrazolo-[3,4-d]pyrimidin-4-yl]-(1-methylpropyl)amine; and 4-(1-methoxymethylpropoxy)-3,6-dimethyl-1-(2,4,6-trimethylphenyl)-1H-pyrazolo[3,4-d]pyrimidine.

For use in the method of the invention, specific compounds of formula II wherein E and D are connected by a double bond, E is —CR$_4$, D is —CR$_{10}$, and Y and A are N, include:

n-butyl-ethyl-[2,5-dimethyl-7-(2,4,6-trimethylphenyl)-7H-pyrrolo[2,3-d]pyrimidin-4-yl]amine;

di-propyl-[2,5-dimethyl-7-(2,4,6-trimethylphenyl)-7H-pyrrolo[2,3-d]pyrimidin-4-yl]amine;

ethyl-n-propyl-[2,5-dimethyl-7-(2,4,6-trimethylphenyl)-7H-pyrrolo[2,3-d]pyrimidin-4-yl]amine;

diethyl-2,5-dimethyl-7-(2,4,6-trimethylphenyl)-7H-pyrrolo[2,3-d]pyrimidin-4-yl]amine;

n-butyl-ethyl-[2,5,6-trimethyl-7-(2,4,6-trimethylphenyl)-7H-pyrrolo[2,3-d]pyrimidin-4-yl]amine 2-{N-n-butyl-N-[2,5-dimethyl-7-(2,4,6-trimethylphenyl)-7H-pyrrolo[2,3-d]pyrimidin-4-yl]amino}-ethanol;

4-(1-ethyl-propyl)-2,5,6-trimethyl-7-(2,4,6-trimethylphenyl)-7H-pyrrolo[2,3-d]pyrimidine;

n-butyl-[2,5-dimethyl-7-(2,4-dimethylphenyl)-7H-pyrrolo[2,3d]pyrimidin-4-yl]amine;

2,5-dimethyl-7-(2,4,6-trimethylphenyl)-7H-pyrrolo[2,3-d]pyrimidyl-4-yl]-(1-ethyl-propyl)amine;

2-[-(4-bromo-2,6-dimethylphenyl)-2,5-dimethyl-7H-pyrrolo[2,3-d]pyrimidin-4-ylamino]-butan-1-ol;

2-(S)-[7-(4-bromo-2,6-dimethylphenyl)-2,5-dimethyl-7H-pyrrolo[2,3-d]pyrimidin-4-ylamino]-butan-1-ol;

4-(1-ethyl-propoxy)-2,5,6-trimethyl-7-(2,4,6-trimethylphenyl)-7H-pyrrolo[2,3-d]pyrimidine;

4-(1-methoxymethyl-propoxy)-2,5,6-trimethyl-7-(2,4,6trimethylphenyl)-7H-pyrrolo[2,3-d]pyrimidine;

4-(1-ethyl-butyl)-2,5,6-trimethyl-7-(2,4,6-trimethylphenyl)-7H-pyrrolo-[2,3-d]pyrimidine;

[7-(4-bromo-2,6-dimethyl-phenyl)-2,5-dimethyl-7H-pyrrolo[2,3-d]pyrimidin-4-yl]-(1-methoxymethyl-propyl)-amine;

2-[7-(2-bromo-4,6-dimethyl-phenyl)-2,5-dimethyl-7H-pyrrolo[2,3-d]pyrimidin-4-ylamino]-butan-1-ol;

2-[7-(4-ethyl-2,6-dimethyl-phenyl)-2,5-dimethyl-7H-pyrrolo[2,3-d]pyrimidin-4-ylamino]-butan-1-ol;

2-[7-(2-ethyl-4,6-dimethylphenyl)-2,5-dimethyl-7H-pyrrolo[2,3-d]pyrimidin-4-ylamino]-butan-1-ol; and 2-[7-(2-fluoromethyl-4,6-dimethylphenyl)-2,5-dimethyl-7H-pyrrolo[2,3-d]pyrimidin-4-ylamino]-butan-1-ol.

The method of the Invention further comprises the treatment of stroke by administering to a mammal, including a human, in need of such treatment a therapeutically effective amount of a compound of formula II, referred to above, or a pharmaceutically acceptable salt thereof, wherein a double bond connects E and D, D is —CR$_{10}$ or N, E is —CR$_4$, and Y and A are N. Compounds of formula III, provided below, are the compounds of formula II wherein a double bond connects E and D, D is —CR$_{10}$ or N, E is —CR$_4$, and Y and A are N. The compounds of formula III are provided below in the claims and are directed to the treatment of stroke.

Whenever reference is made herein to 3- to 8-membered cycloalkyl or 9- to 12-membered bicycloalkyl optionally containing one or two of O, S, or —N—G, it is understood that the oxygen and sulfur atoms are not adjacent to each other in the cycloalkyl or bicycloalkyl ring system. The three membered cycloalkyl optionally contains just one of O, S, or —N—G. An example of a six-membered cycloalkyl having o and NH is morpholinyl.

Whenever R$_2$ or R$_5$ is a heterocyclic group, the attachment of the group is through a carbon atom.

In the compounds of formulas I and II, referred to above, certain animal or acetal moieties may not be sufficiently stable for use in the method of the invention. Such unstable compounds may include, for example, a compound of formula I or II wherein B is —NR$_1$R$_2$ and R$_1$ is —CH(OH)CH$_3$. Such unstable compounds will be apparent to those skilled in the art and do not form part of the invention.

Formulas I and II, referred to above, are Intended to include all stereoisomers (e.g., all geometric and optical isomers) as well as racemates of all individual compounds within the depicted genus.

DETAILED DESCRIPTION OF THE INVENTION

The compounds of formulas I and II, and their pharmaceutically acceptable salts, are readily prepared. The compounds of formula II wherein A, D and Y are N, a double bond connects E and D, and E is —CR$_4$, are prepared by one or more of the synthetic methods referred to in U.S. patent application Ser. No. 08/481,13, referred to above. The compounds of formula II wherein A and Y are N, a double bond connects E and D, E is —CR$_4$, and D is —CR$_{10}$, are prepared by one or more of the synthetic methods referred to in U.S. patent application Ser. No. 08/448,539, referred to above. The compounds of formula II wherein A is —CR$_7$, a double bond connects E and D, E is —CR$_4$, D is N or —CR$_{10}$, and Y is N, are prepared by one or more of the synthetic methods referred to in PCT international application number PCT/IB95/00373, referred to above. The remaining compounds of formula II and the compounds of formula I are prepared by one or more of the synthetic methods referred to in PCT interrational application number PCT/IB95/00439, referred to above.

Pharmaceutically acceptable salts of the compounds of formulas I and II include salts of acidic or basic groups. For example, pharmaceutically acceptable salts include sodium, calcium and potassium salts of acidic groups, such as when the R$_{10}$ substituent is carboxy. Such salts are generally prepared by combining a compound of formula I or II with one molar equivalent of NaOH or KOH in a suitable solvent. Pharmaceutically acceptable acid addition salts of basic groups, such as amino groups, are formed by reacting the base form of a compound of formula I or II with an appropriate acid. Pharmaceutically acceptable salts of basic groups include hydrochloride, hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts. When the salt is of a monobasic acid (e.g., the hydrochloride, the hydrobromide, the p-toluenesulfonate, the acetate), at least one molar equivalent and usually a molar excess of the acid is employed. However, when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration or addition of a non-solvent.

In the method of the invention, the compounds of formulas I and II, and their pharmaceutically acceptable salts, can be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining the active compounds and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type can also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof. Oral administration is generally preferred. However, if the patient is unable to swallow, or oral absorption is otherwise impaired, another route of administration such as suppositories, parenteral (i.m., i.v.), or topical administration will be appropriate.

For parenteral administration, solutions of the active compound in sesame or peanut oil, aqueous propylene glycol, or in sterile aqueous solution can be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

In the method of the invention, the effective dosage for the compounds of formulas I and II, and their pharmaceutically acceptable salts, depends on the intended route of administration and other factors such as age and weight of the patient, as generally known to a physician. The dosage also depends on the illness to be treated. In general, the daily dosage will generally range from about 0.1 to 50 mg/kg of the body weight of the patient to be treated. The daily dosage may be given in a single dose or up to three divided doses. In the prevention of premature birth, the dosage should be administered daily after high levels of corticotropin-releasing hormone have been detected early in pregnancy and then discontinued just prior to the end of the term for normal pregnancy.

The methods for testing the compounds of formulas I and II, and their pharmaceutically acceptable salts, for CRF antagonist activity are as described in Endocrinology, 116, 1653–1659 (1985) and Peptides 10, 179–188 (1989) which determine the binding affinity of a test compound for a CRF receptor. The binding affinities for the active compounds, expressed as IC$_{50}$ values, generally range from about 0.2 nanomolar to about 10 micromolar.

What is claimed is:

1. A method of treating a cardiovascular or heart related disease comprising administering to a mammal in need of such treatment a therapeutically effective amount of a compound of the formula

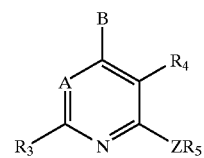

I or a pharmaceutically acceptable salt thereof, wherein
the dashed line represents an optional double bond;
A is N;
B is —NR$_1$R$_2$, —CR$_1$R$_2$R$_{11}$, —C(=CR$_1$R$_{12}$)R$_2$, —NHCR$_{11}$R$_1$R$_2$, —OCR$_{11}$R$_1$R$_2$, —SCR$_{11}$R$_1$R$_2$, —CR$_{11}$R$_2$OR$_1$, —CR$_{11}$R$_2$SR$_2$, —C(S)R$_2$, —NHNR$_1$R$_2$, —CR$_2$R$_{11}$NHR$_1$ or —C(O)R$_2$;
Z is NH, O, S, —N(C$_1$–C$_2$ alkyl) or —CR$_{12}$R$_{13}$, wherein R$_{12}$ and R$_{13}$ are each, independently, hydrogen, trifluoromethyl or methyl, or one of R$_{12}$ and R$_{13}$ is cyano and the other is hydrogen or methyl;
R$_1$ is hydrogen or C$_1$–C$_6$ alkyl which is optionally substituted with one or two substituents independently selected from hydroxy, cyano, nitro, fluoro, chloro, bromo, iodo, $CF_3$, $C_1$–$C_4$ alkoxy, —O—CO—($C_1$–$C_4$ alkyl), —O—CO—NH($C_1$–$C_4$ alkyl), —O—CO—N ($C_1$–$C_4$ alkyl)($C_1$–$C_2$ alkyl), —NH($C_1$–$C_4$ alkyl), —N($C_1$–$C_2$ alkyl)($C_1$–$C_4$ alkyl), —S($C_1$–$C_4$ alkyl), —N($C_1$–$C_4$alkyl)CO($C_1$–$C_4$ alkyl), —NHCO($C_1$–$C_4$ alkyl), —$CO_2$($C_1$–$C_4$ alkyl), —CONH($C_1$–$C_4$ alkyl), —CON($C_1$–$C_4$ alkyl)($C_1$–$C_2$ alkyl), ($C_1$–$C_4$ alkyl)sulfinyl, ($C_1$–$C_4$ alkyl)sulfonyl, and ($C_1$–$C_4$ alkyl)sulfanyl, and wherein said $C_1$–$C_6$ alkyl, $C_1$–$C_4$ alkoxy and the $C_1$–$C_4$ alkyl moieties in the foregoing $R_1$ groups optionally contain one double or triple bond;

$R_2$ is $C_1$–$C_6$ alkyl, heteroaryl, aryl (heteroaryl)$C_1$–$C_4$ alkyl or (aryl)$C_1$–$C_4$ alkyl wherein said aryl and the aryl moiety of said (aryl)$C_1$–$C_4$ alkyl are selected from the group consisting of phenyl and naphthyl, and said heteroaryl and the heteroaryl moiety of said (heteroaryl)$C_1$–$C_4$ alkyl is selected from the group consisting of thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, and benzoxazolyl; or $R^2$ is $C_3$–$C_8$ cycloalkyl or ($C_3$–$C_8$ cycloalkyl)$C_1$–$C_6$ alkyl, wherein one or two of the ring carbons of said cycloalkyl having at least 4 ring members and the cycloalkyl moiety of said ($C_3$–$C_8$ cycloalkyl)$C_1$–$C_6$ alkyl having at least 4 ring members is optionally replaced by an oxygen or sulfur atom or by —$NR_{14}$ wherein $R_{14}$ is hydrogen or $C_1$–$C_4$ alkyl; and wherein each of the foregoing $R_2$ groups is optionally substituted by from one to three substituents independently selected from chloro, fluoro and $C_1$–$C_4$ alkyl, or by one substituent selected from bromo, iodo, cyano, nitro, $C_1$–$C_6$ alkoxy, —O—CO—($C_1$–$C_4$ alkyl), —O—CO—N($C_1$–$C_4$ alkyl)($C_1$–$C_2$ alkyl), —$CO_2$($C_1$–$C_4$ alkyl), ($C_1$–$C_4$ alkyl)sulfanyl, ($C_1$–$C_4$ alkyl) sulfinyl, and ($C_1$–$C_4$ alkyl)sulfonyl, and wherein said $C_1$–$C_6$ alkyl and the $C_1$–$C_4$ alkyl and $C_1$–$C_6$ alkyl moieties of the foregoing $R_2$ groups optionally contain one carbon-carbon double or triple bond;

or $R^1$ and $R^2$ of said —$NR_1R_2$ and said —$CR_1R_2R_{11}$ are taken together to form a saturated 5 to 8 member ring, wherein said ring optionally contains one or two carbon-carbon double bonds, and wherein one or two of the ring carbons is optionally replaced by a heteroatom selected from O, S and N;

$R_3$ is hydrogen, $C_1$–$C_6$ alkyl, fluoro, chloro, bromo, iodo, hydroxy, amino, SH, —NH($C_1$–$C_4$ alkyl), —N($C_1$–$C_4$ alkyl)($C_1$–$C_2$ alkyl), —$CH_2OH$, —$CH_2OCH_3$, —O($C_1$–$C_4$ alkyl), ($C_1$–$C_4$ alkyl)sulfanyl, ($C_1$–$C_4$ alkyl)sulfonyl, or ($C_1$–$C_4$ alkyl)sulfinyl, wherein said $C_1$–$C_6$ alkyl and the $C_1$–$C_4$ alkyl moieties of the foregoing $R_3$ groups optionally contain one double or triple bond and are optionally substituted by from one to three substituents independently selected from hydroxy, amino, $C_1$–$C_3$ alkoxy, —NH($C_1$–$C_2$ alkyl), —N($C_1$–$C_2$)$_2$, —$NHCOCH_3$, fluoro, chloro and $C_1$–$C_3$ thioalkyl;

$R_4$ is hydrogen, $C_1$–$C_6$ alkyl, fluoro, chloro, bromo, iodo, $C_1$–$C_6$ alkoxy, formyl, trifluoromethoxy, —$CH_2OCH_3$, —$CH_2OCH_2CH_3$, —$CH_2CH_2OCH_3$, —$CH_2CF_3$, $CF_3$, amino, nitro, —NH($C_1$–$C_4$ alkyl), —N($CH_3$)$_2$, —$NHCOCH_3$, —$NHCONHCH_3$, ($C_1$–$C_4$ alkyl)sulfanyl, ($C_1$–$C_4$ alkyl)sulfinyl, ($C_1$–$C_4$ alkyl)sulfonyl, cyano, hydroxy, —CO($C_1$–$C_4$ alkyl), —CHO, or —$CO_2$($C_1$–$C_4$ alkyl), wherein said $C_1$–$C_6$ alkyl, $C_1$–$C_6$ alkoxy and the $C_1$–$C_4$ alkyl moieties of the foregoing $R_4$ groups optionally contain one double or triple bond and are optionally substituted with one substituent selected from hydroxy, amino, —$NHCOCH_3$, —NH ($C_1$–$C_2$ alkyl), —N($C_1$–$C_2$ akyl)$_2$, —$CO_2$($C_1$–$C_4$ alkyl), —CO($C_1$–$C_4$ alkyl), $C_1$–$C_3$ alkoxy, ($C_1$–$C_3$ alkyl)sulfanyl, fluoro, chloro, cyano and nitro;

$R_5$ is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, pyridinyl, tetrazolyl, or 3- to 8-membered cycloalkyl or 9- to 12-membered bicycloalkyl, wherein said cycloalkyl and bicycloalkyl optionally contain one or two of O, S or —N—G wherein G is hydrogen, $C_1$–$C_4$ alkyl, $C_1$–$C_4$ alkanoyl, phenyl or benzyl, wherein each of the above $R_5$ groups is optionally substituted by from one to three substituents independenly selected from fluoro, chloro, $C_1$–$C_6$ alkyl, $C_1$–$C_6$ alkoxy and trifluoromethyl, or one substituent selected from bromo, iodo, cyano, nitro, amino, —NH($C_1$–$C_4$ alkyl), —N($C_1$–$C_4$ alkyl)($C_1$–$C_2$ alkyl), —$CO_2$($C_1$–$C_4$ alkyl), —CO($C_1$–$C_4$ alkyl), —$SO_2NH$($C_1$–$C_4$ alkyl), —$SO_2N$($C_1$–$C_4$ alkyl)($C_1$–$C_2$ alky, —$SO_2NH_2$, —$NHSO_2$($C_1$–$C_4$ alkyl), —S($C_1$–$C_4$ alkyl), and —$SO_2$($C_1$–$C_4$ alkyl), wherein said $C_1$–$C_4$ alkyl and $C_1$–$C_6$ alkyl moieties of the foregoing $R_5$ groups optionally contain one double or triple bond and are optionally substituted by one or two substituents independently selected from fluoro, chloro, hydroxy, amino, methylamino, dimethylamino and acetyl; and, $R_{11}$ is hydrogen, hydroxy, fluoro, or methoxy.

2. The method of claim 1 wherein B is —$NR_1R_2$, —$NHCHR_1R_2$, —$CR_1R_2R_{11}$, —$SCHR_1R_2$ or —$OCHR_1R_2$; $R_1$ is $C_1$–$C_6$ alkyl which is optionally substituted with a single hydroxy, fluoro or $C_1$–$C_2$ alkoxy group and optionally contains one carbon-carbon double or triple bond; $R_2$ is benzyl or $C_1$–$C_6$ alkyl which optionally contains one carbon-carbon double or triple bond, wherein said $C_1$–$C_6$ alkyl and the phenyl moiety of said benzyl are optionally substituted with fluoro, $C_1$–$C_2$ alkyl, or $C_1$–$C_2$ alkoxy; and $R_{11}$ is hydrogen or fluoro.

3. The method of claim 1 wherein $R_2$ is (aryl)$C_1$–$C_4$ alkyl in which said aryl moiety is phenyl, thienyl, benzofuranyl, furanyl, benzothienyl, thiazolyl, pyridyl or benzothiazolyl.

4. The method of claim 1 wherein B is $NR_1R_2$ or $CHR_1R_2$ in which $R_1$ and $R_2$ are taken together with N or CH to form a 5- or 6-membered ring optionally having sulfur, oxygen, or, where B is $NR_1R_2$, one more nitrogen in said ring.

5. The method of claim 1 wherein B is —$NHCHR_1R_2$ or —$OCHR_1R_2$, wherein the $CHR_1R_2$ moiety is a 5 or 6-membered ring which optionally contains one oxygen or sulfur.

6. The method of claim 5 wherein B is tetrahydrofuranyl, tetrahydrothiafuranyl or cyclopentanyl.

7. The method of claim 6 wherein B is tetrahydrofuranyl, tetrahydrothienyl or thiazolidinyl.

8. A method of treating a cardiovascular or heart related disease comprising administering to a mammal in need of such treatment a therapeutically effective amount of 4-(1-ethyl-propoxy)-2,5-dimethyl-6-(2,4,6-trimethyl-benzyl)-pyrimide or a pharmaceutically acceptable salt thereof.

9. The method of claim 1 wherein said cardiovascular or heart related disease is selected from hypertension, tachycardia, and congestive heart failure.

10. The method of claim 1 wherein said cardiovascular or heart related disease is congestive heart failure.

11. The method of claim 8 wherein said cardiovascular or heart related disease is selected from hypertension, tachycardia, and a congestive heart failure.

12. The method of claim 8 wherein said cardiovascular or heart disease is congestive heart failure.

13. The method of claim 1 wherein said compound of formula I is selected from the group consisting of 4-(1-ethyl-propoxy)-2,5-dimethyl-6-(2,4,6-trimethyl-benzyl)-pyrimidine;

[2,5-dimethyl-6-(2,4,6-trimethyl-phenoxy)-pyrimidin-4-yl](1-ethyl-propyl)-amine;

(1-ethyl-propyl)-[2-methyl-5-nitro-6-(2,4,6-trimethyl-pyridin-3-yloxy)-pyrimidin-4-yl]-amine;

N-(1-ethyl-propyl)-2-methyl-5-nitro-N'-(2,4,6-trimethyl-pyridin-3-yl)-pyrimidine-4,6-diamine;

4-(1-ethylpropoxy)-2,5-dimethyl-6-(2,4,6-trimethylphenoxy)-pyrimidine;

N-butyl-N-ethyl-2,5-dimethyl-N'-(2,4,6-trimethylphenyl)-pyrimidine-4,6-diamine;

6-(1-ethyl-propoxy)-2-methyl-N4-(2,4,6-trimethyl-phenyl)-pyrimidine-4,5-diamine;

and pharmaceutically acceptable salts of the foregoing compounds.

* * * * *